United States Patent [19]
Entwistle et al.

[11] 3,952,003
[45] Apr. 20, 1976

[54] CERTAIN BENZOTRIAZOLE-4,7-DIONE DERIVATIVES

[75] Inventors: Ian D. Entwistle; Peter J. Williams; Barry R. J. Devlin, all of Sittingbourne, England

[73] Assignee: Shell Oil Company, Houston, Tex.

[22] Filed: Sept. 4, 1973

[21] Appl. No.: 393,769

Related U.S. Application Data

[62] Division of Ser. No. 112,440, Feb. 3, 1971, Pat. No. 3,780,055.

[30] Foreign Application Priority Data

Feb. 17, 1970 United Kingdom................. 7527/70

[52] U.S. Cl............................................. 260/308 B
[51] Int. Cl.²........................................ C07D 249/18

[58] Field of Search ................................ 260/308 B

[56] References Cited
OTHER PUBLICATIONS

Weygand, Chem. Abstracts, Vol. 52, Column 10211 (a), (1958).
Weygand et al., Chem. Abstracts, Vol. 38, Column 1743 (4), (1944).
Wolf, Chem. Abstracts, Vol. 7, pp. 789–790, (1913).

*Primary Examiner*—Alton D. Rollins

[57] ABSTRACT

Novel 1H-indazole-4,7-diones, benzo(d)isoxazole-4,7-diones, benzo(d)triazole-4,7-diones, and benzimidazole-4,7-diones substituted in the 5- and 6- positions, are used for the control of weeds.

2 Claims, No Drawings

CERTAIN BENZOTRIAZOLE-4,7-DIONE DERIVATIVES

This is a division of application Ser. No. 112,400, filed Feb. 2, 1971, now U.S. Pat. No. 3,780,055.

FIELD OF THE INVENTION

This invention relates to the use as herbicides of novel 5,6-disubstituted-1H-indazole-4,7-diones, 5,6-disubstituted-benzo(d)isoxazole-4,7-diones, 5,6-disubstituted-benzo(d)triazole-4,7-diones, and 5,6-di-substituted-benzimidazole-4,7-diones.

DESCRIPTION OF THE PRIOR ART

No pertinent art is known.

SUMMARY OF THE INVENTION

It has now been found that 5,6-disubstituted-1H-indazole-4,7-diones, 5,6-disubstituted-benzo(d)isoxazole-4,7-diones, 5,6-disubstituted-benzo(d)-triazole-4,7-diones, and 5,6-disubstituted-benzimidazole-4,7-diones are novel and useful as short persistence herbicides. In addition, some are useful in controlling weed growth in sugar beets and rice.

DESCRIPTION OF PREFERRED EMBODIMENTS

The novel 4,7-diones of this invention are represented by the following general formula:

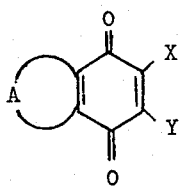

(I)

wherein X and Y each independently represents middle halogen, i.e., chlorine or bromine, an alkoxy group of 1 to 6 carbon atoms, such as ethoxy, an amino group, an amino group mono or di-substituted by alkyl or cycloalkyl of up to 6 carbon atoms, for example methyl, ethyl, isopropyl, sec-butyl or cyclopropyl, or by carbamoyl-substituted alkyl of up to 12 carbon atoms, for example N-methylcarbamoylethyl, or by acyl of up to 6 carbon atoms, such as acetyl or by nitroso, and A, together with the two carbon atoms of the quinone ring to which it is attached represents a pyrazole, isoxazole or triazole ring each substituted by alkyl of 1-6 carbon atoms, for example methyl, isopropyl or trifluoromethyl.

In view of their herbicidal spectra, the following compounds are particularly preferred:

6-isopropylamino-5-(N-acetyl-N-methylamino)-1methyl-1H-indazole-4,7-dione, 6-isopropylamino-1-methyl-5-(N-acetyl-N-methylamino) benzimidazole-4,7-dione.

The novel compounds of the invention wherein X and Y represent halogen and A, together with the two carbon atoms of the quinone ring to which it is attached, represents an alkyl substituted isoxazole or pyrazole ring are prepared by reacting a 2,3-dihalobenzoquinone of the formula:

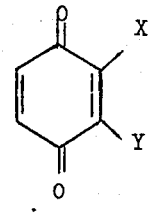

(II)

with either a diazo compound of formula:

R¹CHN₂  (III)

wherein $R^1$ represents a hydrogen atom or an alkyl group, or with a nitrile oxide of formula:

R²CN  O  (IV)

wherein $R^2$ represents an alkyl group, particularly methyl. The reaction with the diazo compound is preferably carried out in an organic solvent such as ether and the reaction with the nitrile oxide may be carried out in an aqueous medium.

Other compounds of Formula I wherein X and Y each represents a halogen atom are obtained by reacting a compound of formula:

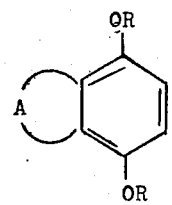

(V)

wherein R represents a hydrogen atom or an alkyl group, preferably methyl, with the appropriate elemental halogen, for example gaseous chlorine or liquid bromine. The reaction is preferably carried out in an organic solvent such as glacial acetic acid or an alcohol, for example methanol.

Those compounds of formula I wherein X and/or Y represents an amino group optionally mono-substituted by alkyl, acyl-substituted alkyl or cycloalkyl may be prepared by reacting a compound of formula I wherein X and/or Y represents a halogen atom with ammonia or the appropriate primary amine, suitably in an organic solvent such as ethanol or methylene chloride.

Those compounds of formula I wherein X and/or Y represents an acyl substituted amino group are prepared by reacting a compound of formula I wherein X and/or Y represents an optionally mono-substituted amino group with a suitable acylating agent such as an acid anhydride, for example acetic anhydride.

Those compounds of Formula I wherein X and/or Y represents a nitrososubstituted amino group are obtained by reacting the corresponding compound wherein X and/or Y represents a mono-substituted amino group, with nitrous acid in acidic aqueous solution.

As mentioned above the compounds of the invention exhibit herbicidal properties and are of particular interest as pre-emergence selective herbicides for combating weeds in sugar beet and rice crops.

The invention is further illustrated in the following examples. For certain of the compounds given below, which have non-identical groups at the 5- and 6-positions, the preparative procedure may give rise to the formation of the isomeric compound in which the positions of the two groups have been reversed. In most cases it is not known with certainty whether a single isomer or isomer mixture is obtained. For convenience, therefore, the compounds have been named as single isomers.

EXAMPLE I 5,6-Dichloro-1-methyl-1H-indazole-4,7-dione

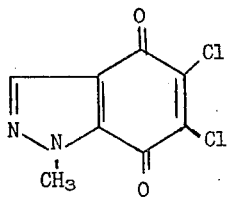

2,3-Dichlorobenzoquinone (22 grams) was added portionwise to a stirred solution of diazomethane (14 grams) in ether (500 milliliters) maintained at a temperature below 15°C. A pale yellow solid separated out from the solution, and this was filtered off and dried to yield the desired product having a melting point of 176°–177°C.

Analysis: Calculated for $C_8H_4N_2O_2Cl_2$: C, 41.7; H, 1.7; N, 12.1; Cl, 30.7%. Found: C, 42,3; H, 1.7; N, 12.2; Cl, 30.5%.

EXAMPLE II

6-Chloro-5-cyclopropylamino-1-methyl-1H-indazole-4,7-dione 5,6-Dichloro-1-methyl-1H-indazole-4,7-dione (10 grams prepared as in Example I) and cyclopropylamine (10 grams) in ethanol (50 milliliters) were stirred together at room temperature for 30 minutes. The precipitate formed was filtered off and dried to yield the desired product as a red solid having a melting point of 175°–176°C.

Analysis: Calculated for $C_{11}H_{10}N_3O_2Cl$: C, 52,5; H, 4.0; N, 16.7%. Found: C, 52.5; H, 4.6; N, 16.4%.

EXAMPLE III

6-Chloro-5-(N-acetyl-N-cyclopropylamino)-1-methyl-1H-indazole-4,7-dione

6-Chloro-5-cyclopropylamino-1-methyl-1H-indazole-4,7-dione (3 grams prepared as in Example II) was added to acetic anhydride (10 milliliters) containing a few drops of concentrated sulphuric acid. The mixture was stirred at 50°C for 15 minutes and then poured into ice-water. The aqueous mixture was extracted with methylene chloride and the extracts washed with aqueous sodium bicarbonate solution and dried. The solvent was then removed under reduced pressure to give a yellow solid which on recrystallization from ethanol gave the desired product having a melting point of 171°C.

Analysis: Calculated for $C_{13}H_{12}N_3O_3Cl$: C, 53.2; H, 4.1; N, 14.3%. Found: C, 53.3; H, 4.5; N, 13.8%.

EXAMPLE IV

6-Cyclopropylamino-5-(N-acetyl-N-cyclopropylamino)-1-methyl-1H-indazole-4,7-dione 6-Chloro-5-(N-acetyl-N-cyclopropylamino)-1-methyl-1H-indazole-4,7-dione (2 grams prepared as in Example III) and cyclopropylamine (2 grams) in ethanol (25 milliliters) were heated together under reflux for 10 minutes. The solvent was then removed under reduced pressure and the residual red oil purified by chromatography on alumina using methylene chloride as eluant to yield the desired product having a melting point of 75°–78°C.

Analysis: Calculated for $C_{16}H_{18}N_4O_3$: C, 61.1; H, 5,8; N,17.8%. Found: C, 60.4; H, 5,8; N, 17.4%.

EXAMPLE V

Reaction of 6-chloro-5-(N-acetyl-N-isopropylamino)-1-methyl-1H-indazole-4,7-dione with isopropylamine a. 6-Chloro-5-(N-acetyl-N-isopropylamino)-1-methyl-1H-indazole-4,7-dione (3 grams prepared by a similar method to that described in Example III) and isopropylamine (3 grams) in ethanol (25 milliliters) were heated together under reflux for 10 minutes. On cooling the reaction mixture a yellow-orange solid crystallized out, which was filtered off and dried to yield 6-ethoxy-5-(N-acetyl-N-isopropylamino)-1-methyl-1H-indazole-4,7-dione having a melting point of 154°–155°C.

Analysis: Calculated For $C_{15}H_{19}N_3O_4$: C, 59.0; H, 6.3; N, 13.8%. Found: C, 59.0; H, 6.3; N, 13.7%.

b. 6-Chloro-5-(N-acetyl-N-isopropylamino)-1-methyl-1H-indazole-4,-7-dione (3 grams) and isopropylamine (3 grams) in methylene chloride (25 milliliters) were heated under reflux for 15 minutes. The solvent was then removed under reduced pressure and the residue recrystallized from ethanol to give 6-isopropylamino-5-(N-acetyl-N-isopropylamino)-1-methyl-1H-indazole-4,7-dione as a red solid having a melting point of 123°–126°C.

Analysis: Calculated for $C_{16}H_{22}N_4O_3$: C, 60.4; H, 7.0; N, 17.6%. Found: C, 60.3; H, 6.7; N, 17.5%.

EXAMPLE VI

6-Chloro-1-methyl-5-(Nitroso-N-methylamino)indazole-4,7-dione

6-Chloro-5-methylamino-1-methylindazole-4,7-dione (4.5 grams) in 30 % hydrochloric acid (50 milliliters was stirred at 0°C and treated dropwise with a solution of sodium nitrite (3.0 grams) in water (20 milliliters). After 1 hour the orange solid which had separated out was collected, washed with water and dried over silica gel to yield the desired product having a melting point of 124°–125°C (with decomposition).

Analysis: Calculated for $C_8H_7N_4O_3Cl$: C, 42.4; H, 2.8; N, 22.0 %. Found: C, 42.7; H, 2.9; N, 21.9%.

EXAMPLE VII 5,6-Dichloro-3-methylbenzo(d)isoxazole-4,7-dione

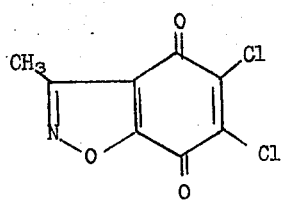

A solution of acetonitrile oxide was prepared by passing chlorine (10.8 grams) over 30 minutes into a stirred suspension of acetaldoxime (9 grams) and sodium bicarbonate (25.2 grams) in water at 0°C was added 2,3-dichlorobenzoquinone (17.7 grams) portionwise over 15 minutes. The mixture was stirred at 0°-5°C for 2 hours and then extracted with methylene chloride. The dried extracts were evaporated to dryness under reduced pressure and the residue recrystallized from ethanol to give the desired product as yellow crystals having a melting point of 214°-215°C.

Analysis: Calculated for $C_8H_3NO_3Cl_2$: C, 41.5; H, 1.3; N, 6.0%. Found: C, 41.9; H, 1.5; N, 6.0%.

EXAMPLE VIII 5,6-Dichloro-1-methylbenzo(d)triazole-4,7-dione

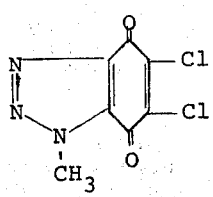

4,7-Dimethoxybenzo(d)triazole (1.2 grams) in glacial acetic acid was warmed to 50°C and chlorine gas was passed into the solution for 1 hour. The solution was then poured into water and extracted with methylene chloride. The dried organic extracts were evaporated to dryness under reduced pressure and the residue treated with ethanol to yield to desired product as a yellow crystalline solid having a melting point of 254°-255°C.

Analysis: Calculated for $C_7H_3N_3O_2Cl_2$: C, 36.2; H, 1.3; N, 18.1; Cl, 30.6%. Found: C, 36.2; H, 1.3; N, 17.9; Cl, 30.9%.

EXAMPLE IX 5,6-Dibromo-1-methylbenzimidazole-4,7-dione

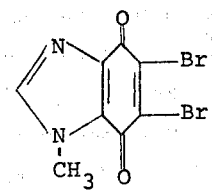

4,7-Dimethoxy-1-methylbenzimidazole (3.0 grams) was added portionwise to a solution of bromine (10.0 grams) in methanol (20 milliliters) over a period of 10 minutes. The mixture was stirred for 1 hour at room temperature then poured into water and the excess bromine removed by bubbling air through the mixture. The yellow precipitate obtained was filtered off and recrystallized from ethanol to give the desired product having a melting point of 250°C (with decomposition).

Analysis: Calculated for $C_8H_4N_2O_2Br_2$: C, 30.0; H, 1.3; N, 8.8%. Found: C, 30.6; H, 1.4; N, 8.6%.

EXAMPLE X

Following procedures similar to those given in the previous examples further compounds were prepared, whose physical characteristics and analysis are set out in Table I.

TABLE 1

| COMPOUND | MELTING POINT °C | ANALYSIS | |
|---|---|---|---|
| 5-amino-6-chloro-1-methyl-1H-indazole-4,7-dione | 285–286 | Calculated for $C_8H_6N_3O_2Cl$<br>Found | C 45.5; H 2.8; N 19.9; Cl 16.8%<br>C 45.9; H 3.1; N 19.6; Cl 16.7% |
| 6-chloro-5-isopropylamino-1-methyl-1H-indazole-4,7-dione | 142–143 | Calculated for $C_{11}H_{12}N_3O_2Cl$<br>Found | C 52.1; H 4.7; N 16.6; Cl 14.0%<br>C 52.1; H 4.7; N 16.4; Cl 14.3% |
| 6-isopropylamino-5-(N-acetyl-N-methylamino)-1-methyl-1H-indazole-4,7-dione | 188–189 | Calculated for $C_{14}H_{18}N_4O_3$<br>Found | C 57.9; H 6.3; N 19.3%<br>C 57.2; H 6.0; N 19.0% |
| 6-chloro-5-(N-acetyl-N-isopropylamino)-1-methyl-1H-indazole-4,-7-dione | 143–144 | Calculated for $C_{13}H_{14}N_3O_3Cl$<br>Found | C 52.9; H 4.7; N 14.2%<br>C 52.5; H 4.6; N 14.0% |
| 5-(N-acetyl-N-methylamino)-6-(1-(N-methylcarbamoyl)ethyl)amino-1-methyl-1H-indazole-4,7-dione | 182–183 | Calculated for $C_{15}H_{19}N_5O_4$<br>Found | C 54.0; H 5.8; N 21.0%<br>C 54.1; H 6.2; N 20.4% |
| 6-cyclopropylamino-5-(N-acetyl-N-methylamino)-1-methyl-1H-indazole-4,7-dione | 167–168 | Calculated for $C_{14}H_{16}N_4O_3$<br>Found | C 58.3; H 5.6; N 19.4%<br>C 58.2; H 5.9; N 19.2% |
| 6-cyclopropylamino-5-(N-acetyl-N-ethylamino)-1-methyl-1H-indazole-4,7-dione | 162–163 | Calculated for $C_{15}H_{18}N_4O_3$<br>Found | C 59.6; H 6.0; N 18.5%<br>C 59.6; H 6.3; N 18.0% |
| 6-chloro-5-ethylamino-1-methyl-1H-indazole-4,7-dione | 147 | Calculated for $C_{10}H_{10}N_3O_2Cl$<br>Found | C 50.1; H 4.2; N 17.5%<br>C 50.2; H 4.2; N 17.4% |
| 6-methylamino-5-(N-acetyl-N-methylamino)-1-methyl-1H-indazole-4,7-dione | 209–210 | Calculated for $C_{12}H_{14}N_4O_3$<br>Found | C 54.9; H 5.4; N 21.3%<br>C 54.4; H 5.6; N 20.9% |
| 6-methylamino-5-(N-acetyl-N-ethylamino)-1-methyl-1H-indazole-4,7-dione | 163–165 (dec) | Calculated for $C_{13}H_{16}N_4O_3$<br>Found | C 56.5; H 5.8; N 20.3%<br>C 56.8; H 6.0; N 20.0% |
| 5-amino-6-chloro-3-methylbenzo(d)isoxazole-4,7-dione | 222–223 | Calculated for $C_8H_5N_2O_3Cl$<br>Found | C 45.2; H 2.4; N 13.2; Cl 16.7%<br>C 45.6; H 2.6; N 13.1; Cl 16.7% |
| 5-(N-acetylamino)-6-chloro-3-methylbenzo(d)isoxazole-4,7-dione | 183–184 | Calculated for $C_{10}H_7N_2O_4Cl$<br>Found | C 47.1; H 2.8; N 11.0%<br>C 47.1; H 2.7; N 11.1% |
| 6-chloro-5-methylamino-3-methylbenzo(d)isoxazole-4,7-dione | 195–196 | Calculated for $C_9H_7N_2O_3Cl$<br>Found | C 47.6; H 3.1; N 12.4%<br>C 47.8; H 3.2; N 12.1% |
| 6-isopropylamino-5-(N-acetyl-N-methylamino)-3-methylbenzo(d)-isoxazole-4,7-dione | 186–187 | Calculated for $C_{14}H_{17}N_3O_4$<br>Found | C 57.7; H 5.9; N 14.4%<br>C 57.9; H 5.9; N 14.0% |
| 6-chloro-5-isopropylamino-3-methylbenzo(d)isoxazole-4,7-dione | 133–134 | Calculated for $C_{11}H_{11}N_2O_3$<br>Found | C 51.9; H 4.3; N 11.0%<br>C 52.0; H 4.3; N 10.7% |
| 6-chloro-5-methylamino-1-methylbenzotriazole-4,7-dione | 196–197 | Calculated for $C_8H_7N_4O_2Cl$<br>Found | C 42.4; H 3.1; N 24.7%<br>C 42.1; H 3.3; N 24.8% |

TABLE 1-continued

| COMPOUND | MELTING POINT °C | ANALYSIS | |
|---|---|---|---|
| 6-isopropyl-1-methyl-5-(N-acetyl-N-methylamino)-benzotriazole-4,7 dione | 164–165 (dec) | Calculated for $C_{13}H_{17}N_5O_3$<br>Found | C 53.6; H 5.9%<br>C 53.6; H 6.3% |
| 6-chloro-5-isopropylamino-1-methylbenzotriazole-4,7-dione | 106–107 | Calculated for $C_{10}H_{11}N_4O_4Cl$<br>Found | C 47.2; H 4.3; N 22.0; Cl 14.0%<br>C 46.8; H 4.4; N 21.8; Cl 13.6% |
| 6-isopropylamino-5-(N-acetyl-N-isopropylamino)-1-methyl-benzotriazole-4,7-dione | 179–181 (dec) | Calculated for $C_{15}H_{21}N_5O_3$<br>Found | C 56.4; H 6.6; N 21.9%<br>C 56.7; H 6.9; N 21.8% |
| 6-isopropylamino-1-methyl-5-(N-acetyl-N-methylamino) benzimidazole-4,7-dione | 159–165 | Calculated for $C_{14}H_{18}N_4O_3$<br>Found | C 57.9; H 6.3; N 19.3%<br>C 57.8; H 6.4; N 19.3% |
| 6-chloro-5-isopropylamino-1-methyl-benzimidazole-4,7-dione | 169–170 | Calculated for $C_{11}H_{12}N_3O_2Cl$<br>Found | C 51.8; H 4.7; N 16.4; Cl 14.0%<br>C 51.9; H 4.8; N 16.2; Cl 13.8% |
| 5,6-dibromo-2-trifluoromethylbenzimidazole-4,7-dione | 237–238 | Calculated for $C_8HN_2O_2Br_2F_3$<br>Found | C 25.7; H 0.7; N 7.5%<br>C 25.8; H 1.1; N 7.2% |
| 6-bromo-5-methylamino-2-trifluoromethylbenzimidazole-4,7-dione | >230 dec | Calculated for $C_9H_5N_3O_2Br\ F_3$<br>Found | C 33.3; H 1.5; N 12.9%<br>C 33.7; H 1.7; N 12.6% |
| 5,6-dichlorobenzimidazole-4,7-dione | >330 dec | Calculated for $C_7H_2N_2O_2Cl_2$<br>Found | C 38.7; H 0.9; N 12.8; Cl 32.2%<br>C 38.9; H 1.0; N 12.4; Cl 32.7% |
| 6-isopropylamino-5-(N-acetyl-N-methylamino)-2-trifluoromethylbenzimidazole-4,7-dione | >200 dec | Calculated for $C_{14}H_{15}N_4O_3F_3$<br>Found | C 48.8; H 4.3; N 16.2%<br>C 48.7; H 4.5; N 16.0% |
| 5,6-dichloro-1-methylbenzimidazole-4,7-dione | >260 dec | Calculated for $C_8H_4N_2O_2Cl_2$<br>Found | C 41.6; H 1.7; N 12.1%<br>C 41.6; H 1.7; N 11.8% |
| 1-methyl-6-(N-acetyl-N-methylamino)-5-S-butylamino benzimidazole-4,7-dione | 164–165 | Calculated for $C_{15}H_{20}N_4\ O_3$<br>Found | C 59.2; H 6.6; N 18.4%<br>C 58.9; H 6.6; N 18.2% |
| 5,6-dichloro-1-isopropylbenzimidazole-4,7-dione | 146–148 | Calculated for $C_{10}H_8N_2O_2Cl_2$<br>Found | C 46.4; H 3.1; N 10.8%<br>C 46.8; H 3.5; N 10.4% |

EXAMPLE XI

Herbicidal Activity

To evaluate their herbicidal activity, the compounds of the invention were tested using as a representative range of plants: maize, Zea mays (Mz); rice, Oryza sativa (R); barnyard grass, Echinchloa crusgalli (BG); pea, Pisum sativum (P); linseed, Linum usitatissium (L); mustard, Sinapis alba (M); and sugar beet, Beta vulgaris (SB). In the tests on one of the compounds rice was replaced by oat, Avena sativa and barnyard grass by ryegrass Lolium perenne.

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz. soil drench and foliar spray tests. In the soil drench tests the soil in which seedling plants of the above species were growing, was drenched with a liquid formulation containing a compound of the invention, and in the foliar spray tests the seedling plants were sprayed with such a formulation.

The soil used in the tests was a steam-sterilized, modified John Innes Compost mixture in which half the peat, by loose bulk, had been replaced by vermiculite.

The formulations used in the tests were prepared by diluting with water and solutions of the compounds in acetone containing 0.4% by weight of an alkylphenol-/ethylene oxide condensate available under the trade name Triton X-155. In the soil spray and foliar spray tests the acetone solutions were diluted with an equal volume of water and the resulting formulations applied at two dosage levels corresponding to 10 and 1 kilograms of active material per hectare respectively in a volume equivalent to 400 liters per hectare. In the soil drench tests one volume of the acetone solution was diluted to 155 volumes with water and the resulting formulation applied at one dosage level equivalent to 10 kilogram of active material per hectare in a volume equivalent to approximately 3,000 liters per hectare.

In the pre-emergence tests untreated sown soil and in the post-emergence tests untreated soil bearing seedling plants were used as controls.

The herbicidal effects of the compounds were assessed visually seven days after spraying the foilage and drenching the soil and eleven days after spraying the soil, and were recorded on a 0–9 scale. A rating 0 indicates no effect on the treated plants, a rating 2 indicates a reduction in fresh weight of stem and leaf of the plants of approximately 25%, a rating 5 indicates a reduction of approximately 55%, a rating 9 indicates a reduction of 95% etc.

The results of the tests are set out in Table 2–5.

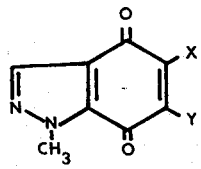

Table 2

| | COMPOUND | | POST-EMERGENCE (PLANTS) | | | | | | | | | | | | | | |
|---|---|---|---|---|---|---|---|---|---|---|---|---|---|---|---|---|---|
| | | DOSAGE | SOIL DRENCH | | | | | | | DOSAGE | FOLIAR SPRAY | | | | | | |
| X | Y | kg/ha | MZ | R | BG | P | L | M | SB | kg/ha | MZ | R | BG | P | L | M | SB |
| NH CH(CH$_3$)$_2$ | Cl | 10 | — | — | — | — | — | — | — | 10 | — | 1* | 8** | — | 9 | 9 | — |
| | | | | | | | | | | 1 | — | 0* | 5** | — | 6 | 8 | — |

Table 2-continued

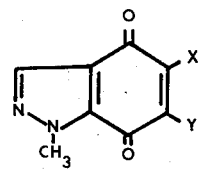

| COMPOUND | | DOSAGE | POST-EMERGENCE (PLANTS) SOIL DRENCH | | | | | | | DOSAGE | FOLIAR SPRAY | | | | | | |
|---|---|---|---|---|---|---|---|---|---|---|---|---|---|---|---|---|---|
| X | Y | kg/ha | MZ | R | BG | P | L | M | SB | kg/ha | MZ | R | BG | P | L | M | SB |
| N(COCH$_3$)CH$_3$ | NH CH(CH$_3$)$_2$ | 10 | 9 | 8 | 8 | 9 | 9 | 9 | 7 | 10 | 9 | 9 | 9 | 9 | 9 | 9 | 9 |
|  |  |  |  |  |  |  |  |  |  | 1 | 5 | 2 | 6 | 5 | 9 | 9 | 7 |
| COCH$_3$ N cyclopropyl | Cl | 10 | 0 | 0 | 2 | 0 | 1 | 0 | 0 | 10 | 3 | 0 | 8 | 1 | 8 | 9 | 8 |
|  |  |  |  |  |  |  |  |  |  | 1 | 2 | — | 4 | 0 | 2 | 6 | 4 |
| N(COCH$_3$)CH$_3$ | NH CH CONHCH$_3$ CH$_3$ | 10 | 2 | 1 | 1 | 4 | 9 | 3 | 2 | 10 | 7 | 9 | 9 | 9 | 9 | 9 | 9 |
|  |  |  |  |  |  |  |  |  |  | 1 | 3 | 5 | 8 | 7 | 9 | 9 | 6 |
| N(COCH$_3$)CH$_3$ | NH cyclopropyl | 10 | 3 | 3 | 7 | 4 | 8 | 8 | 5 | 10 | 7 | 7 | 9 | 7 | 9 | 9 | 9 |
|  |  |  |  |  |  |  |  |  |  | 1 | 5 | 7 | 9 | 5 | 9 | 9 | 9 |
| COCH$_3$ N cyclopropyl | NH cyclopropyl | 10 | 9 | 4 | 7 | 9 | 9 | 9 | 8 | 10 | 8 | 9 | 9 | 9 | 9 | 9 | 9 |
|  |  |  |  |  |  |  |  |  |  | 1 | 4 | 5 | 9 | 6 | 9 | 9 | 9 |
| N(COCH$_3$)CH(CH$_3$)$_2$ | OC$_2$H$_5$ | 10 | 3 | 3 | 1 | 3 | 4 | 1 | 0 | 10 | 5 | 1 | 9 | 4 | 9 | 9 | 9 |
|  |  |  |  |  |  |  |  |  |  | 1 | 1 | 1 | 7 | 3 | 9 | 9 | 8 |
| N(COCH$_3$)C$_2$H$_5$ | NH cyclopropyl | 10 | 8 | 7 | 7 | 7 | 9 | 8 | 7 | 10 | 9 | 9 | 9 | 9 | 9 | 9 | 9 |
|  |  |  |  |  |  |  |  |  |  | 1 | 6 | 7 | 9 | 5 | 9 | 9 | 9 |
| NHC$_2$H$_5$ | Cl | 10 | 0 | 0 | 3 | 0 | 0 | 0 | 0 | 10 | 2 | 2 | 9 | 5 | 9 | 9 | 9 |
|  |  |  |  |  |  |  |  |  |  | 1 | 0 | 1 | 9 | 2 | 9 | 9 | 7 |
| N(COCH$_3$)CH$_3$ | NHCH$_3$ | 10 | 1 | 0 | 5 | 3 | 8 | 8 | 3 | 10 | 6 | 6 | 9 | 6 | 9 | 9 | 9 |
|  |  |  |  |  |  |  |  |  |  | 1 | 4 | 2 | 8 | 2 | 8 | 9 | 9 |
| N(COCH$_3$)C$_2$H$_5$ | NHCH$_3$ | 10 | 1 | 4 | 8 | — | 9 | 8 | 7 | 10 | 3 | 6 | 9 | — | 9 | 9 | 9 |
|  |  |  |  |  |  |  |  |  |  | 1 | 2 | 5 | 9 | — | 9 | 9 | 9 |
| N(COCH$_3$)CH(CH$_3$)$_2$ | NH CH(CH$_3$)$_2$ | 10 | 9 | 9 | 9 | — | 9 | 9 | 9 | 10 | 9 | 8 | 9 | — | 9 | 9 | 9 |
|  |  |  |  |  |  |  |  |  |  | 1 | 4 | 5 | 9 | — | 9 | 9 | 9 |
| N(NO)CH$_3$ | Cl | 10 | 0 | 0 | 0 | 0 | 0 | 0 | 0 | 10 | 1 | 1 | 7 | 2 | 9 | 9 | 9 |
|  |  |  |  |  |  |  |  |  |  | 1 | 0 | 1 | 4 | 0 | 5 | 4 | 3 |

| COMPOUND | | PRE-EMERGENCE (SEEDS) SOIL SPRAY | | | | | | |
|---|---|---|---|---|---|---|---|---|
| X | Y | MZ | R | BG | P | L | M | SB |
| NH CH(CH$_3$)$_2$ | Cl | — | 0* | 7** | — | 5 | 4 | — |
|  |  | — | — | 1** | — | 3 | 1 | — |
| N(COCH$_3$)CH$_3$ | NH CH(CH$_3$)$_2$ | 9 | 9 | 9 | 6 | 9 | 9 | 8 |
|  |  | 7 | 8 | 7 | 3 | 6 | 8 | 0 |
| COCH$_3$ N cyclopropyl | Cl | 0 | 7 | 0 | 0 | 0 | 1 | 0 |
|  |  | — | 0 | — | — | — | 0 | — |
| N(COCH$_3$)CH$_3$ | NH CH CONHCH$_3$ CH$_3$ | 5 | 9 | 7 | 1 | 9 | 9 | 8 |
|  |  | 1 | 8 | 0 | 0 | 3 | 8 | 0 |
| N(COCH$_3$)CH$_3$ | NH cyclopropyl | 8 | 9 | 9 | 9 | 9 | 9 | 9 |
|  |  | 1 | 9 | 5 | 2 | 5 | 8 | 0 |
| COCH$_3$ N cyclopropyl | NH cyclopropyl | 9 | 9 | 9 | 9 | 9 | 9 | 9 |
|  |  | 6 | 8 | 6 | 5 | 6 | 9 | 0 |
| N(COCH$_3$)CH(CH$_3$)$_2$ | OC$_2$H$_5$ | 0 | 7 | 6 | 0 | 2 | 6 | 2 |
|  |  | — | 1 | 1 | — | 0 | 0 | 0 |
| N(COCH$_3$)C$_2$H$_5$ | NH cyclopropyl | 8 | 9 | 9 | 9 | 9 | 9 | 9 |
|  |  | 2 | 7 | 4 | 1 | 3 | 3 | 0 |
| NHC$_2$H$_5$ | Cl | 0 | 3 | 4 | 0 | 0 | 3 | 2 |
|  |  | — | 0 | 0 | — | — | 0 | 0 |
| N(COCH$_3$)CH$_3$ | NHCH$_3$ | 0 | 9 | 9 | 3 | 9 | 9 | 9 |
|  |  | — | 1 | 2 | 0 | 0 | 4 | 0 |
| N(COCH$_3$)C$_2$H$_5$ | NHCH$_3$ | 5 | 8 | 9 | 8 | 9 | 9 | 9 |
|  |  | 0 | 2 | 7 | 2 | 7 | 9 | 0 |
| N(COCH$_3$)CH(CH$_3$)$_2$ | NH CH(CH$_3$)$_2$ | 9 | 9 | 9 | 9 | 9 | 9 | 9 |
|  |  | 5 | 3 | 9 | 3 | 9 | 9 | 2 |
| N(NO)CH$_3$ | Cl | 3 | 4 | 7 | 0 | 2 | 3 | 4 |
|  |  | 0 | 0 | 0 | — | 0 | 0 | 0 |

*result obtained with oat, Avena sativa
**result obtained with ryegrass, Lolium perenne Table 3

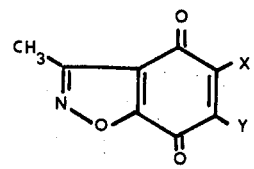

| COMPOUND | | DOSAGE | POST-EMERGENCE (PLANTS) SOIL DRENCH | | | | | | | DOSAGE | FOLIAR SPRAY | | | | | | |
|---|---|---|---|---|---|---|---|---|---|---|---|---|---|---|---|---|---|
| X | Y | kg/ha | MZ | R | BG | P | L | M | SB | kg/ha | MZ | R | BG | P | L | M | SB |
| NH₂ | Cl | 10 | — | — | — | — | — | — | — | 10 | — | 2 | 8 | — | 8 | 8 | — |
|  |  |  |  |  |  |  |  |  |  | 1 | — | 2 | 8 | — | 7 | 7 | — |
| NHCOCH₃ | Cl | 10 | 2 | 1 | 7 | 2 | 7 | 9 | 9 | 10 | 1 | 3 | 9 | 3 | 8 | 9 | 9 |
|  |  |  |  |  |  |  |  |  |  | 1 | 1 | 2 | 6 | 1 | 8 | 9 | 9 |
| N(COCH₃)CH₃ | NH CH(CH₃)₂ | 10 | 5 | 3 | 2 | 3 | 2 | 8 | 8 | 10 | 2 | 2 | 9 | 6 | 9 | 9 | 9 |
|  |  |  |  |  |  |  |  |  |  | 1 | 1 | 1 | 6 | 2 | 6 | 9 | 9 |
| NHCH(CH₃)₂ | Cl | 10 | 0 | 0 | 4 | 0 | 0 | 4 | 7 | 10 | 0 | 0 | 4 | 2 | 8 | 5 | 4 |
|  |  |  |  |  |  |  |  |  |  | 1 | — | — | 1 | 0 | 6 | 7 | 2 |

| COMPOUND | | PRE-EMERGENCE (SEEDS) SOIL SPRAY | | | | | | |
|---|---|---|---|---|---|---|---|---|
| X | Y | MZ | R | BG | P | L | M | SB |
| NH₂ | Cl | — | 0 | 4 | — | 2 | 0 | — |
|  |  | — | — | 0 | — | 0 | — | — |
| NHCOCH₃ | Cl | 0 | 8 | 8 | 4 | 3 | 9 | 9 |
|  |  | — | 0 | 0 | 0 | 0 | 0 | 0 |
| N(COCH₃)CH₃ | NH CH(CH₃)₂ | 2 | 9 | 9 | 4 | 4 | 9 | 8 |
|  |  | 0 | 6 | 0 | 0 | 0 | 0 | 0 |
| NHCH(CH₃)₂ | Cl | 0 | 0 | 0 | 0 | 0 | 0 | 0 |
|  |  | — | — | — | — | — | — | — |

Table 4

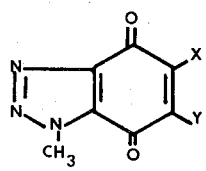

| COMPOUND | | DOSAGE | POST-EMERGENCE (PLANTS) SOIL DRENCH | | | | | | | DOSAGE | FOLIAR SPRAY | | | | | | |
|---|---|---|---|---|---|---|---|---|---|---|---|---|---|---|---|---|---|
| X | Y | kg/ha | Mz | R | BG | P | L | N | SB | kg/ha | Mz | R | BG | P | L | M | SB |
| N(COCH₃)CH₃ | NH CH(CH₃)₂ | 10 | 6 | 6 | 5 | 7 | 9 | 9 | 9 | 10 | 9 | 7 | 9 | 7 | 9 | 9 | 5 |
|  |  |  |  |  |  |  |  |  |  | 1 | 2 | 5 | 8 | 7 | 9 | 9 |  |
| NH CH(CH₃)₂ | Cl | 10 | — | — | — | — | — | — | — | 10 | — | 2 | 9 | — | 9 | 9 | — |
|  |  |  |  |  |  |  |  |  |  | 1 | — | 1 | 5 | — | 4 | 8 | — |
| N(COCH₃)CH(CH₃)₂ | NH CH(CH₃)₂ | 10 | 8 | 4 | 4 | 3 | 6 | 8 | 6 | 10 | 8 | 9 | 9 | 8 | 9 | 9 | 9 |
|  |  |  |  |  |  |  |  |  |  | 1 | 6 | 4 | 2 | 4 | 9 | 9 | 9 |

| COMPOUND | | PRE-EMERGENCE (SEEDS) SOIL SPRAY | | | | | | |
|---|---|---|---|---|---|---|---|---|
| X | Y | Mz | R | BG | P | L | M | SB |
| N(COCH₃)CH₃ | NH CH(CH₃)₂ | 6 | 9 | 9 | 6 | 9 | 9 | 9 |
|  |  | 0 | 7 | 2 | 1 | 3 | 0 | 0 |
| NH CH(CH₃)₂ | Cl | — | 0 | 0 | — | 0 | 0 | — |
|  |  | — | — | — | — | — | — | — |
| N(COCH₃)CH(CH₃)₂ | NH CH(CH₃)₂ | 9 | 9 | 9 | 9 | 9 | 9 | 9 |
|  |  | 8 | 8 | 8 | 1 | 6 | 9 | 9 |

Table 5

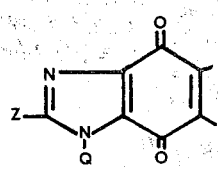

| COMPOUND | | | | | | POST-EMERGENCE (PLANTS) | | | | | | | | | | | | | |
|---|---|---|---|---|---|---|---|---|---|---|---|---|---|---|---|---|---|---|---|
| | | | | DOSAGE | | SOIL DRENCH | | | | | | DOSAGE | | FOLIAR SPRAY | | | | | |
| X | Y | Z | Q | kg/ha | Mz | R | BG | P | L | M | SB | kg/ha | Mz | R | BG | P | L | M | SB |
| N(COCH$_3$)CH$_3$ | NH CH(CH$_3$)$_2$ | H | CH$_3$ | 10 | 9 | 9 | 9 | 9 | 7 | 9 | 5 | 10 | 9 | 9 | 9 | 9 | 9 | 9 | 9 |
| | | | | | | | | | | | | 1 | 6 | 6 | 6 | 8 | 9 | 9 | 9 |
| NH CH(CH$_3$)$_2$ | Cl | H | CH$_3$ | 10 | 0 | 0 | 1 | 0 | 0 | 0 | 0 | 10 | 0 | 0 | 3 | 2 | 9 | 8 | 3 |
| | | | | | | | | | | | | 1 | — | — | 3 | 1 | 6 | 6 | 2 |

| COMPOUND | | | | PRE-EMERGENCE (SEEDS) | | | | | | |
|---|---|---|---|---|---|---|---|---|---|---|
| | | | | SOIL SPRAY | | | | | | |
| X | Y | Z | Q | Mz | R | BG | P | L | M | SB |
| N(COCH$_3$)CH$_3$ | NH CH(CH$_3$)$_2$ | H | CH$_3$ | 9 | 9 | 9 | 8 | 9 | 9 | 8 |
| | | | | 8 | 6 | 9 | 3 | 2 | 7 | 1 |
| NH CH(CH$_3$)$_2$ | Cl | H | CH$_3$ | 0 | 5 | 9 | 0 | 0 | 7 | 1 |
| | | | | — | 0 | 0 | — | — | 0 | 0 |

The novel compounds can be formulated as herbicidal compositions comprising a carrier or a surface-active agent, or both a carrier and a surface-active agent, together with as active ingredient, at least one substituted 1,4-quinone derivative of the invention.

The term "carrier" as used herein means a material, which may be inorganic or organic and of synthetic or natural origin, with which the active compound is mixed or formulated to facilitate its application to the plant, seed, soil or other object to be treated, or its storage, transport or handling. The carrier may be a solid or a fluid. Any of the material usually applied in formulating herbicides may be used as carrier.

Suitable solid carriers are natural and synthetic clays and silicates for example natural silicas such as diatomacious earths; magnesium silicates, for example, talcs; magnesium aluminum silicates, for example, attapulgites and vermiculites; aluminum silicates, for example, kaolinites, montmorillinites and micas; calcium carbonates; calcium sulphate; synthetic hydrated silicon oxides and synthetic calcium or aluminum silicates; elements such as for example, carbon and sulphur; natural and synthetic resins such as for example, coumarone resins, polyvinyl chloride and styrene polymers and copolymers; solid polychlorophenols; bitumens; waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octyl-cresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for exmaple sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain, in addition to solid carrier, 3–10% by weight of a dispersing agent and, where necessary, 0–10% by weight of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% by weight of toxicant. Granules are usually prepared to have a size between 10 and 100 BS mesh, and may be manufactured by agglomeration or impregnation techniques. Generally, granules will contain ½–25% by weight toxicant and 0–10% by weight of additives such as stabilizers, slow release modifiers and binding agents. Emulsifiable concentrates usually contain, in addition to the solvent and, when necessary, co-solvent, 10–50% weight/volume toxicant, 2–20% weight/volume emulsifiers and 0–20% weight/volume of appropriate additives such as stabilizers, penetrants and corrosion inhibitors. Suspension concentrates are compounded so as to obtain a stable, non-sedimenting, flowable product and usually contain 10–75% by weight toxicant, 0.5–15% by weight of dispersing agents, 0.1–10% by weight of suspending agents such as protective colloids and thixotropic agents, 0–10% by weight of appropriate additives such as defoamers, corrosion inhibitors, stabilizers, penetrants and stickers and as carrier, water or an organic liquid in which the toxicant is substantially insoluble; certain organic solids or inorganic salts may be dissolved in the carrier to assist in preventing sedimentation or as antifreeze agents for water.

The compositions of the invention may contain other ingredients, for example, protective colloids such as gelatin, glue, casein, gums, cellulose ethers, and polyvinyl alcohol; thixotropic agents, e.g., bentonites, sodium polyphosphates; stabilizers such as ethylene diamine tetra-acetic acid, urea, triphenyl phosphate; other herbicides or pesticides; and stickers, for example non-volatile oils.

Aqueous dispersion and emulsions, for example, compositions obtained by diluting a wettable powder or an emulsifiable concentrate according to the invention with water, also lie within the scope of the present invention. The said emulsions may be of the water-in-oil or of the oil-in-water type, and may have a thick "mayonnaise"-like consistency.

We claim as our invention:

1. A substituted 1,4-quinone of the formula

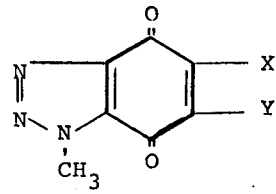

wherein Y is Cl or isopropylamino and, when Y is Cl, X is Cl, methylamino or isopropylamino and, when Y is isopropylamino, X is acetylmethylamino or acetylisopropylamino.

2. A substituted 1.4-quinone derivative according to claim 1 wherein X is acetylmethylamino, Y is isopropylamino.

* * * * *